United States Patent [19]

Sager et al.

[11] Patent Number: 5,262,528
[45] Date of Patent: Nov. 16, 1993

[54] CDNA PROBE DIFFERENTIATING NORMAL AND CANCER TISSUES

[75] Inventors: Ruth Sager, Brookline; Sam W. Lee; Catherine Tomasetto, both of Boston, all of Mass.

[73] Assignee: Dana-Farber Cancer Institute, Inc., Boston, Mass.

[21] Appl. No.: 662,198

[22] Filed: Feb. 28, 1991

[51] Int. Cl.$^5$ .................. C12N 15/11; C12N 1/21
[52] U.S. Cl. .................. 536/24.31; 435/172.3; 435/252.3
[58] Field of Search ............ 536/27, 24.31; 530/300, 530/828, 387.7; 435/172.3, 240.2, 252.3

[56] References Cited

U.S. PATENT DOCUMENTS

| 4,423,145 | 12/1983 | Stampfer et al. | 435/32 |
| 4,816,404 | 3/1989 | Suciu-Foca et al. | 435/70.21 |
| 5,049,662 | 9/1991 | Steeg | 435/6 |

OTHER PUBLICATIONS

PCT Search Report in the corresponding PCT Application No. PCT/US92/01625.
Chen et al., Proc. Natl. Acad. Sci. USA 86:7204–7207, 1989.

Primary Examiner—Robert A. Wax
Assistant Examiner—Stephen Walsh
Attorney, Agent, or Firm—Fish & Richardson

[57] ABSTRACT

Nucleic acid encoding clone 19 gene product, and protein which interacts specifically with an antibody specific to the gene product of clone 19.

2 Claims, No Drawings

CDNA PROBE DIFFERENTIATING NORMAL AND CANCER TISSUES

The invention was made with support from the National Institute of Health, specifically Grant No. CA39814. The U.S. government has rights in the invention.

BACKGROUND OF THE INVENTION

This invention relates to diagnosis and treatment of cancers, particularly, solid tumors.

Sager, 246 *Science* 1406, 1989, discusses tumor suppressor genes. The loss of tumor suppressor genes, or their inactivation, is oncogenic. That is, the loss of DNA encoding a tumor suppressor gene product, or the lowering of expression of a tumor suppressor gene gives rise to a cancerous condition. Sager generally describes the identification of such tumor suppressor genes. In particular, Sager describes the process of subtractive hybridization as a general method for recovering genes that are expressed in normal cells but not in closely related tumor cells. Sager further describes the isolation of three clones by subtractive hybridization of normal and cancerous mammary cells. The genes corresponding to these clones are expressed by all normal mammary epithelial cells, but not by any primary mammary tumors or mammary tumor cell lines. One such gene encodes keratin 5, which is said to be a valuable marker to distinguish normal and primary tumor cells in culture. Also identified is a gene encoding fibronectin, and a third gene identified as NB-1. Tumor suppressor genes are proposed to play a key role in cancer protection, and it is suggested that tumor suppressor genes provide a vast untapped resource for anti-cancer therapy.

SUMMARY OF THE INVENTION

This invention features a novel gene and its gene product which are useful in methods for identifying cancerous cells present in a human, particularly in solid tumors. The gene and gene product are also useful for identifying drugs useful for treatment of such cancer cells, and for treatment of the cancerous condition. Unlike prior methods, the invention provides a means for identifying cancer cells at an early stage of development, such that premalignant cells can be identified prior to spreading throughout the human body. This allows early detection of potentially cancerous conditions, and treatment of those cancerous conditions prior to spread of the cancerous cells throughout the body, or prior to development of an irreversible cancerous condition.

Thus, in a first aspect, the invention features nucleic acid encoding clone 19 gene product; preferably, nucleic acid identical to clone 19. By clone 19 is meant that nucleic acid shown in nucleic acid sequence 1 between bases 48 and 338. The gene product is the corresponding amino acid sequence.

In a related aspect the invention features protein which interacts specifically (i.e., only with the gene product of clone 19 and not with other proteins found in human cells which normally contain clone 19 gene product) with an antibody specific to the gene product of clone 19; preferably, the protein is the gene product of clone 19.

Other features and advantages of the invention will be apparent from the following description of the preferred embodiments thereof, and from the claims.

DESCRIPTION OF THE PREFERRED EMBODIMENTS

The following is a specific example of a subtractive hybridization procedure used to screen a cDNA library for clone 19. This example is not limiting in the invention and those of ordinary skill in the art will recognize that many variations to this method can be used with equivalent efficacy in identifying useful tumor suppressor genes.

EXAMPLE 1

Identification and Isolation of Clone 19

In this example the medium, DFCI-1, described by Band and Sager, 86 *Proc. Natl. Acad. Sci., USA* 1249, 1989 was used because of its ability to support similar growth of both normal and tumor-derived human mammary epithelial cells. cDNA rather than genomic DNA was used for screening by negative selection since the cDNAs are smaller and easier to manipulate than their genomic counterpart, and are present in multiple copies. Recovery of such cDNAs allows their use as probes to isolate the equivalent genomic DNA. Further the cDNA can be expressed in a expression vector to produce the tumor suppressor gene product, and thus allow production of antibodies to that product for use in the methods described herein.

The normal cells used were derived from a strain 76N established from discarded reduction mammoplasty tissue as described by Band and Sager, supra. These cells are diploid and senesce after 15-20 passages. The tumor cells were derived from an aneuploid cell line established from a pleural effusion as described by Band et al., 1 *Genes Chromosomes, and Cancer* 48, 1989 and Band et al., 50 *Cancer Research* 7351, 1990. However, any pair of cells used for subtractive hybridization can be derived from any single individual and substituted as described below. Primary tumor cells or metastic cells can be used. In this example, both parental cell populations were grown in DFCI-1 medium at similar population doubling times of about 30 hours. These cells were harvested at 70% confluency directly into 4M guanidium isothiocyanate, 0.5M sodium citrate, and 0.1M $\beta$-mercaptoethanol for RNA preparation. Total RNA was extracted from the cells by lysis in the guanidium isothiocyanate mixture, and poly(a)+RNA purified by two cycles of affinity chromatography on oligo(dT) cellulose by standard technique. The cDNA was synthesized using Moloney murine leukemia virus reverse transcriptase from Bethesda Research Laboratories with an oligodeoxynucleotide oligo(dT)$_{12-18}$ as a primer.

The $^{32}$P pre-labeled SS cDNA from 76N cells was hybridized with a 10-fold excess of tumor poly(A)+ mRNA from 21MT-2 cells. 500 ng fibronectin (FN) mRNA, prepared by in vitro transcription was added to subtract out FN cDNA, which is present at high abundance in the mRNA of the normal cells. The hybridization reaction mixture was loaded onto a hydroxylapatite column maintained at 60° C. and eluted with 0.1M phosphate buffer (pH 6.8). After rerunning the effluent through the column three times, the effluent was collected and rehybridized as above (2nd subtraction) without added FN mRNA. The final effluent was concentrated to 100 $\mu$l, a sample was removed for quantitation, and the rest frozen for subsequent screening.

cDNA from 76N poly(A)+ RNA was used to produce a recombinant library in the phagemid lambda Zap II (Stratagene Corp., La Jolla, Calif.) by procedures recommended by the vender. The 76N library was screened by differential hybridization using the $^{32}P$ random-primer labelled subtracted cDNA probe against the tumor specific cDNA. After a secondary screening the differentially expressed clones were isolated, and the inserts were amplified by PCR from phage using T3 and T7 sequences as primers. After gel electrophoresis, the PCR products were purified by phenol/chloroform extraction from agarose and $^{32}P$ random-primer labelled for RNA northern analysis.

Total RNA (20 ug) was heat denatured at 68° C. for 15-20 min. followed by electrophoresis in 1.2% agarose-formaldehyde gels and transferred to nylon membranes (Zeta-probe, BioRad); prehybridization and hybridization were performed as described by Haskill et al., 87 *Proc. Natl. Acad. Sci, USA* 7732, 1990. Sequencing of cloned DNA was performed either directly or on exonuclease III-deleted derivatives. These deletion derivatives were generated using a Promega Erase-a-Base kit but can be generated by using other standard technique. Sequencing was carried out by a dideoxy chain termination method with T7 DNA polymerase (Pharmacia). Parallel reactions were also performed with dGTP analogs (Pharmacia) when necessary to resolve sequence compressions.

In one subtraction, 50 clones were recovered. After two rounds of screening, seven different clones showed unique or highly preferential expression in normal cells compared to tumor cells. The clones were identified by northern hybridization using standard techniques. The size range of mRNAs varied from 0.6 kb to almost 5 kb.

A clone including DNA termed clone 19 represents a gene expressed in normal mammary epithelial cell strains but not in tumor-derived cell lines. The DNA sequence (and corresponding amino acid sequence of the gene product) of clone 19 is shown as nucleotide sequence 1 below. The gene product corresponds to that amino acid sequence approximately between bases 46-338. Sequence comparisons have shown that it is a member of the S100 gene family, encoding small $Ca^{++}$ binding proteins (about 10 kD) with diverse functions. These proteins have two "EF hands", domains where $Ca^{2+}$ is bound, in contrast to calmodulin proteins which have four. The S100 beta protein is a major constituent of glial cells, whereas related proteins are expressed in differentiated but not in undifferentiated PC 12 (rat pheochromocytoma) cells. Clone 19 is also related in structure to the small regulatory subunit of calpactin, p11. MRP8 and MRP14 are also related and are S100 proteins expressed by macrophages during chronic inflammation. Calabretta et al., 261 *J. Biol. Chem.* 12628, 1986. Another related protein, calcyclin, has been found in serum-induced cycling cells, but not in quiescent cells, and in leukocytes from CML patients. A related mouse protein is also cell cycle induced. The possibility that calcyclin expression might be cancer related, is particularly interesting in view of our evidence that clone 19 is not expressed in breast tumor cells. Clone 19 appears to be negatively regulated in tumors in contrast to calcyclin. Other related proteins are described by Kligman and Hilt 13 TIBS 437, 1988.

Although the mRNA corresponding to the clone 19 gene is absent, the gene is present in southern blots of tumor cells. (Small deletions or rearrangements would not have been detected.)

Clinical Applications

Clone 19 is useful because the corresponding gene (clone 19 gene) has not been lost in tumor cells, and is therefore available for up-regulation by drugs or equivalent treatment. Restoration of gene function by regulatory intervention offers new opportunities in the design of novel drugs for cancer therapy.

Clone 19 gene is useful for early diagnosis and prognosis, which are especially pressing needs in breast cancer where the course of the disease is so unpredictable. It is thus useful as a diagnostic marker.

Clone 19, and closely related nucleic acid, can be used for diagnosis and treatment of cancer. For example, it is particularly useful for identification of cancerous cells in solid tumors, such as in breast cancer. Once a lump is detected in a mammogram, or by other means in a breast, a portion of that lump may be removed and analyzed by northern analysis or by in situ hybridization using the cloned gene (or antibodies to the gene product produced by standard technique) to determine whether the level of expression of the clone 19 gene is normal or at a reduced level. If it is at a reduced level, this will indicate that the cells in that lump are cancerous or pre-cancerous and appropriate steps may be taken to either remove or treat those cells in vivo.

Similarly, routine diagnosis can be obtained in a manner similar to a papsmear in which cells are taken from a human and tested with clone 19 or antibodies to the gene product of clone 19. Such testing will allow earlier diagnosis of cancerous conditions than has previously been possible.

Those of ordinary skill in this art will recognize that the northern analysis and in situ hybridization can be carried out by any of a number of standard techniques. For example, the DNA of clone 19 or its equivalent cDNA may be used as a probe for RNA produced by the clone 19 gene in cells to be tested. Similarly, DNA which hybridizes to the RNA produced by such a gene can also be used.

The cDNA or its equivalent may be placed in expression vectors to cause production of clone 19 gene product which may be purified and used to isolate polyclonal or monoclonal antibodies to that gene product. Those particular antibodies which are specific for hybridization with the gene product can be identified by standard procedure. Generally, it is preferred that a specific monoclonal antibody be identified so that a large amount of that antibody can be readily produced and used in diagnostic procedures. Again, immune complex formation of antibodies with clone 19 gene product is performed by standard methodology such as by western blot or in situ hybridization.

The clone 19 gene can be used to identify useful drugs for treatment of cancers. This may be performed by standard procedure by culturing cells which include the clone 19 gene (which are either expressed at normal or subnormal levels) and treating those cells with a variety of drugs to determine which drug increases the level of expression of clone 19 gene product within those cells. It is preferred that a cancerous cell be used in such a procedure since the increased level of expression of the gene product will be more readily detected. Identification of the increase in gene expression can be analyzed by standard northern or in situ analysis or by antibody testing. Similarly, rather than looking for expression of the clone 19 gene, the related increase in a function of that gene may be detected by standard techniques.

Once the appropriate drug is identified it may be administered to humans which are identified as containing cells having a reduced level of the clone 19 gene product. This may be either by direct administration of the drug at the tumor site or by more systemic treatment with the drug.

Other embodiments are within the following claims.

COMPUTER SUBMISSION OF DNA AND AMINO ACID SEQUENCES (1) GENERAL INFORMATION:
- (i) APPLICANT: Sager, Ruth; Sam W. Lee; Catherine Tomasetto
- (ii) TITLE OF INVENTION: CANCER DIAGNOSIS AND THERAPY
- (iii) NUMBER OF SEQUENCES: 1
- (iv) CORRESPONDENCE ADDRESS:
  - (A) ADDRESSEE: Fish & Richardson
  - (B) STREET: 225 Franklin Street
  - (C) CITY: Boston
  - (D) STATE: Massachusetts
  - (E) COUNTRY: U.S.A.
  - (F) ZIP: 02110-2804
- (v) COMPUTER READABLE FORM:
  - (A) MEDIUM TYPE: 3.5" Diskette, 1.44 Mb storage
  - (B) COMPUTER: IBM PS/2 Model 50Z or 55SX
  - (C) OPERATING SYSTEM: IBM P.C. DOS (Version 3.30)
  - (D) SOFTWARE: WordPerfect (Version 5.0)
- (vi) CURRENT APPLICATION DATA:
  - (A) APPLICATION:
  - (B) FILING DATE:
  - (C) CLASSIFICATION:
- (vii) PRIOR APPLICATION DATA:
  Prior applications total, including application described below:
  - (A) APPLICATION NUMBER:
  - (B) FILING DATE:
- (viii) ATTORNEY/AGENT INFORMATION:
  - (A) NAME: Richard J. Warburg, Esq.
  - (B) REGISTRATION NUMBER: 32,327
  - (C) REFERENCE/DOCKET NUMBER: 00530-048001
- (ix) TELECOMMUNICATION INFORMATION:
  - (A) TELEPHONE: (617) 542-5070
  - (B) TELEFAX: (617) 542-8906
  - (C) TELEX: 200154

2. INFORMATION FOR SEQ. NO: 1:
   - (i) SEQUENCE CHARACTERISTICS:
     - (A) LENGTH: 450
     - (B) TYPE: nucleic acid
     - (C) STRANDEDNESS: double
     - (D) TOPOLOGY: linear
   - (ii) SEQUENCE DESCRIPTION: 1:

```
GCACGAGCTG    GGTCTGTCTC    TGCCACCTGG    TCTGCCACAG    ATCCATG
ATG TGC AGT TCT CTG GAG CAG GCG CTG GCT GTG CTG GTC ACT ACC TTC
 M   C   S   S   L   E   Q   A   L   A   V   L   V   T   T   F
CAC AAG TAC TCC TGC CAA GAG GGC GAC AAG TTC AAG CTG AGT AAG GGG
 H   K   Y   S   C   Q   E   G   D   K   F   K   L   S   K   G
GAA ATG AAG GAA CTT CTG CAC AAG GAG CTG CCC AGC TTT GTG GGG GAG
 E   M   K   E   L   L   H   K   E   L   P   S   F   V   G   E
AAA GTG GAT GAG GAG GGG CTG AAG AAG CTG ATG GGC AAC CTG GAT GAG
 K   V   D   E   E   G   L   K   K   L   M   G   N   L   D   E
AAC AGT GAC CAG CAG GTG GAC TTC CAG GAG TAT GCT GTT TTC CTG GCA
 N   S   D   Q   Q   V   D   F   Q   E   Y   A   V   F   L   A
CTC ATC ACT GTC ATG TGC AAT GAC TTC TTC CAG GGC TGC CCA GAC CGA
 L   I   T   V   M   C   N   D   F   F   Q   G   C   P   D   R
CCC TGA
 P   *
AGCAGAACTC    TTGACTCCCT    GCCATGGATC    TCTTGGGCCC    AGGACTGTTG    ATGCCTTTGA
GTTTTGTATT    CAATAAACTT    TTTTTGTCTG    TTGAAAAAAA    AAAAAAAAAA    A
```

---

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:

(A) LENGTH: 452
(B) TYPE: nucleic acid
(C) STRANDEDNESS: double
(D) TOPOLOGY: linear (xi) SEQUENCE DESCRIPTION: SEQ ID NO: 1:

```
GCACGAGCTG GGTCTGTCTC TGCCACCTGG TCTGCCACAG ATCCATG ATG TGC AGT         56
                                                     Met Cys Ser
                                                      1

TCT CTG GAG CAG GCG CTG GCT GTG CTG GTC ACT ACC TTC CAC AAG TAC       104
Ser Leu Glu Gln Ala Leu Ala Val Leu Val Thr Thr Phe His Lys Tyr
     5              10                  15

TCC TGC CAA GAG GGC GAC AAG TTC AAG CTG AGT AAG GGG GAA ATG AAG       152
Ser Cys Gln Glu Gly Asp Lys Phe Lys Leu Ser Lys Gly Glu Met Lys
 20              25                  30                  35

GAA CTT CTG CAC AAG GAG CTG CCC AGC TTT GTG GGG GAG AAA GTG GAT       200
Glu Leu Leu His Lys Glu Leu Pro Ser Phe Val Gly Glu Lys Val Asp
                 40                  45                  50

GAG GAG GGG CTG AAG AAG CTG ATG GGC AAC CTG GAT GAG AAC AGT GAC       248
Glu Glu Gly Leu Lys Lys Leu Met Gly Asn Leu Asp Glu Asn Ser Asp
             55                  60                  65

CAG CAG GTG GAC TTC CAG GAG TAT GCT GTT TTC CTG GCA CTC ATC ACT       296
Gln Gln Val Asp Phe Gln Glu Tyr Ala Val Phe Leu Ala Leu Ile Thr
         70                  75                  80

GTC ATG TGC AAT GAC TTC TTC CAG GGC TGC CCA GAC CGA CCC                338
Val Met Cys Asn Asp Phe Phe Gln Gly Cys Pro Asp Arg Pro
     85                  90                  95

TGAAGCAGAA CTCTTGACTC CCTGCCATGG ATCTCTTGGG CCCAGGACTG TTGATGCCTT       398

TGAGTTTTGT ATTCAATAAA CTTTTTTGT CTGTTGAAAA AAAAAAAAA AAAA              452
```

(2) INFORMATION FOR SEQ ID NO: 2:

(i) SEQUENCE CHARACTERISTICS:
(A) LENGTH: 97
(B) TYPE: amino acid
(C) STRANDEDNESS:
(D) TOPOLOGY: linear (xi) SEQUENCE DESCRIPTION: SEQ ID NO: 2:

```
Met Cys Ser Ser Leu Glu Gln Ala Leu Ala Val Leu Val Thr Thr Phe
 1               5                  10                  15

His Lys Tyr Ser Cys Gln Glu Gly Asp Lys Phe Lys Leu Ser Lys Gly
                 20                  25                  30

Glu Met Lys Glu Leu Leu His Lys Glu Leu Pro Ser Phe Val Gly Glu
             35                  40                  45

Lys Val Asp Glu Glu Gly Leu Lys Lys Leu Met Gly Asn Leu Asp Glu
         50                  55                  60

Asn Ser Asp Gln Gln Val Asp Phe Gln Glu Tyr Ala Val Phe Leu Ala
 65                  70                  75                  80

Leu Ile Thr Val Met Cys Asn Asp Phe Phe Gln Gly Cys Pro Asp Arg
                 85                  90                  95

Pro
```

We claim:
1. Isolated DNA comprising a nucleotide sequence substantially identical to SEQ ID NO:1.
2. A cell useful for the production of a cloned DNA molecule, said cell comprising the isolated DNA of claim 1.

* * * * *

UNITED STATES PATENT AND TRADEMARK OFFICE
CERTIFICATE OF CORRECTION

PATENT NO. : 5,262,528

DATED : November 16, 1993

INVENTOR(S) : RUTH SAGER, SAM W. LEE, CATHERINE TOMASETTO

It is certified that error appears in the above-identified patent and that said Letters Patent is hereby corrected as shown below:

Title page, item [56], insert the following references:

--Cowan et al., 1986, Proc. Natl. Acad. Sci. USA 83:9328.
Yaswen et al., 1990, Proc. Natl. Acad. Sci. USA 87:7360.
Trask et al., 1990, Proc. Natl. Acad. Sci. USA 87:2319.
Sager, 1989, Science 246:1406.
Calabretta et al., 1986, J. Biol. Chem. 261:12628.
Band et al., 1990 Cancer Res. 50:7351.
Moscow et al., 1989, Cancer Res. 49:1422.
Zhang and Nicholson, 1989, J. Cell. Biol. 109:3391.
Lersch and Fuchs, 1988, Molec. Cell. Biol. 8:486.
Band and Sager, 1989, Proc. Natl. Acad. Sci. USA 86:1249.
Kligman and Hilt, 1988, TIBS 13:437.
Band et al., 1989, Genes. Chromosomes & Cancer 1:48.--

UNITED STATES PATENT AND TRADEMARK OFFICE
CERTIFICATE OF CORRECTION

PATENT NO. : 5,262,528

DATED : November 16, 1993

INVENTOR(S) : RUTH SAGER, SAM W. LEE, CATHERINE TOMASETTO

It is certified that error appears in the above-identified patent and that said Letters Patent is hereby corrected as shown below:

Delete the COMPUTER SUBMISSION OF DNA AND AMINO ACID SEQUENCES at column 5, lines 4-64. Also delete the portion of the SEQUENCE LISTING shown in column 5, lines 66-70 and replace it with the following:

SEQUENCE LISTING (1) GENERAL INFORMATION:

(i) APPLICANT: Sager, Ruth
    Lee, Sam W.
    Tomasetto, Catherine (ii) TITLE OF INVENTION: CANCER DIAGNOSIS AND THERAPY (iii) NUMBER OF SEQUENCES: 2

(iv) CORRESPONDENCE ADDRESS:

(A) ADDRESSEE: Fish & Richardson
        (B) STREET: 225 Franklin Street
        (C) CITY: Boston
        (D) STATE: Massachusetts
        (E) COUNTRY: U.S.A.
        (F) ZIP: 02110-2804

(v) COMPUTER READABLE FORM:

(A) MEDIUM TYPE: 3.5" Diskette, 1.44 Mb
        (B) COMPUTER: IBM PS/2 Model 50Z or 55SX
        (C) OPERATING SYSTEM: IBM P.C. DOS (Version 3.30)
        (D) SOFTWARE: WordPerfect (Version 5.0)

UNITED STATES PATENT AND TRADEMARK OFFICE
CERTIFICATE OF CORRECTION

PATENT NO.   : 5,262,528

DATED        : November 16, 1993

INVENTOR(S)  : RUTH SAGER, SAM W. LEE, CATHERINE TOMASETTO

It is certified that error appears in the above-identified patent and that said Letters Patent is hereby corrected as shown below:

(vi) CURRENT APPLICATION DATA:

(A) APPLICATION NUMBER: 07/662,198
        (B) FILING DATE:        February 28, 1991
        (C) CLASSIFICATION:

(vii) PRIOR APPLICATION DATA:

(A) APPLICATION NUMBER:
        (B) FILING DATE:

(viii) ATTORNEY/AGENT INFORMATION:

(A) NAME:                Fraser, Janis K.
        (B) REGISTRATION NUMBER: 34,819
        (C) REFERENCE/DOCKET NUMBER: 00530/049001

(ix) TELECOMMUNICATION INFORMATION:

(A) TELEPHONE:   (617) 542-5070
        (B) TELEFAX:     (617) 542-8906
        (C) TELEX:             200154

UNITED STATES PATENT AND TRADEMARK OFFICE
CERTIFICATE OF CORRECTION

PATENT NO. : 5,262,528
DATED : November 16, 1993
INVENTOR(S) : RUTH SAGER, SAM W. LEE, CATHERINE TOMASETTO It is certified that error appears in the above-indentified patent and that said Letters Patent is hereby corrected as shown below:

(2) INFORMATION FOR SEQUENCE IDENTIFICATION NUMBER: 1:

(i) SEQUENCE CHARACTERISTICS:

Signed and Sealed this

First Day of November, 1994

Attest:

BRUCE LEHMAN

Attesting Officer     Commissioner of Patents and Trademarks